US010752565B2

United States Patent
Nair et al.

(10) Patent No.: US 10,752,565 B2
(45) Date of Patent: Aug. 25, 2020

(54) PROCESSES FOR PRODUCING TRIFLUOROIODOMETHANE

(71) Applicant: Honeywell International Inc., Morris Plains, NJ (US)

(72) Inventors: Haridasan K. Nair, Williamsville, NY (US); Rajiv Banavali, Morristown, NJ (US); Rajiv Ratna Singh, Getzville, NY (US)

(73) Assignee: Honeywell International Inc., Morris Plains, NJ (US)

(*) Notice: Subject to any disclaimer, the term of this patent is extended or adjusted under 35 U.S.C. 154(b) by 0 days.

(21) Appl. No.: 16/549,389

(22) Filed: Aug. 23, 2019

(65) Prior Publication Data

US 2020/0062678 A1    Feb. 27, 2020

Related U.S. Application Data

(60) Provisional application No. 62/722,553, filed on Aug. 24, 2018.

(51) Int. Cl.
| | |
|---|---|
| *C07C 17/363* | (2006.01) |
| *C07C 19/16* | (2006.01) |
| *B01J 21/18* | (2006.01) |
| *C07C 17/087* | (2006.01) |
| *C07C 17/383* | (2006.01) |

(52) U.S. Cl.
CPC .............. *C07C 17/087* (2013.01); *B01J 21/18* (2013.01); *C07C 17/363* (2013.01); *C07C 19/16* (2013.01); *C07C 17/383* (2013.01)

(58) Field of Classification Search
None
See application file for complete search history.

(56) References Cited

U.S. PATENT DOCUMENTS

| | | | |
|---|---|---|---|
| 3,154,382 | A | 10/1964 | Gerald |
| 5,532,411 | A | 7/1996 | Braun et al. |
| 5,574,192 | A | 11/1996 | Vanderpuy et al. |
| 7,132,578 | B1 | 11/2006 | Mukhopadhyay et al. |
| 7,196,236 | B2 | 3/2007 | Mukhopadhyay et al. |
| 8,084,653 | B2 | 12/2011 | Tung et al. |

(Continued)

FOREIGN PATENT DOCUMENTS

CN      102992943 A   *   3/2013

OTHER PUBLICATIONS

CN-102992943-A, English translation, Mar. 27, 2013, pp. 1-12 (Year: 2013).*

(Continued)

*Primary Examiner* — Medhanit W Bahta
(74) *Attorney, Agent, or Firm* — Faegre Drinker Biddle & Reath LLP

(57) ABSTRACT

The present disclosure provides a gas-phase process for producing trifluoroiodomethane, the process comprising providing a reactant stream comprising hydrogen iodide and trifluoroacetyl halide selected from the group consisting of trifluoroacetyl chloride, trifluoroacetyl fluoride, trifluoroacetyl bromide, and combinations thereof, and reacting the reactant stream in the presence of a catalyst at a temperature from about 200° C. to about 600° C. to produce a product stream comprising the trifluoroiodomethane.

25 Claims, 1 Drawing Sheet

(56) References Cited

U.S. PATENT DOCUMENTS

2006/0122440 A1* 6/2006 Mukhopadhyay .... C07C 17/093
  570/152
2009/0137852 A1* 5/2009 Yang ........................ B01J 23/04
  570/137

OTHER PUBLICATIONS

Wikipedia "Atmosphere of Earth", pp. 1-14.*
Date, H. "Properties of electron swarms in CF3I" Appl. Phys. Lett 95, 101504 (2009) (Year: 2009).*
Haszeldine, R. N. (1951). 124. The Reactions of Metallic Salts of Acids with Halogens. Part I. The Reaction of Metal Trifluoroacetates with Iodine, Bromine, and Chlorine. Journal of the Chemical Society, pp. 584-587.

* cited by examiner

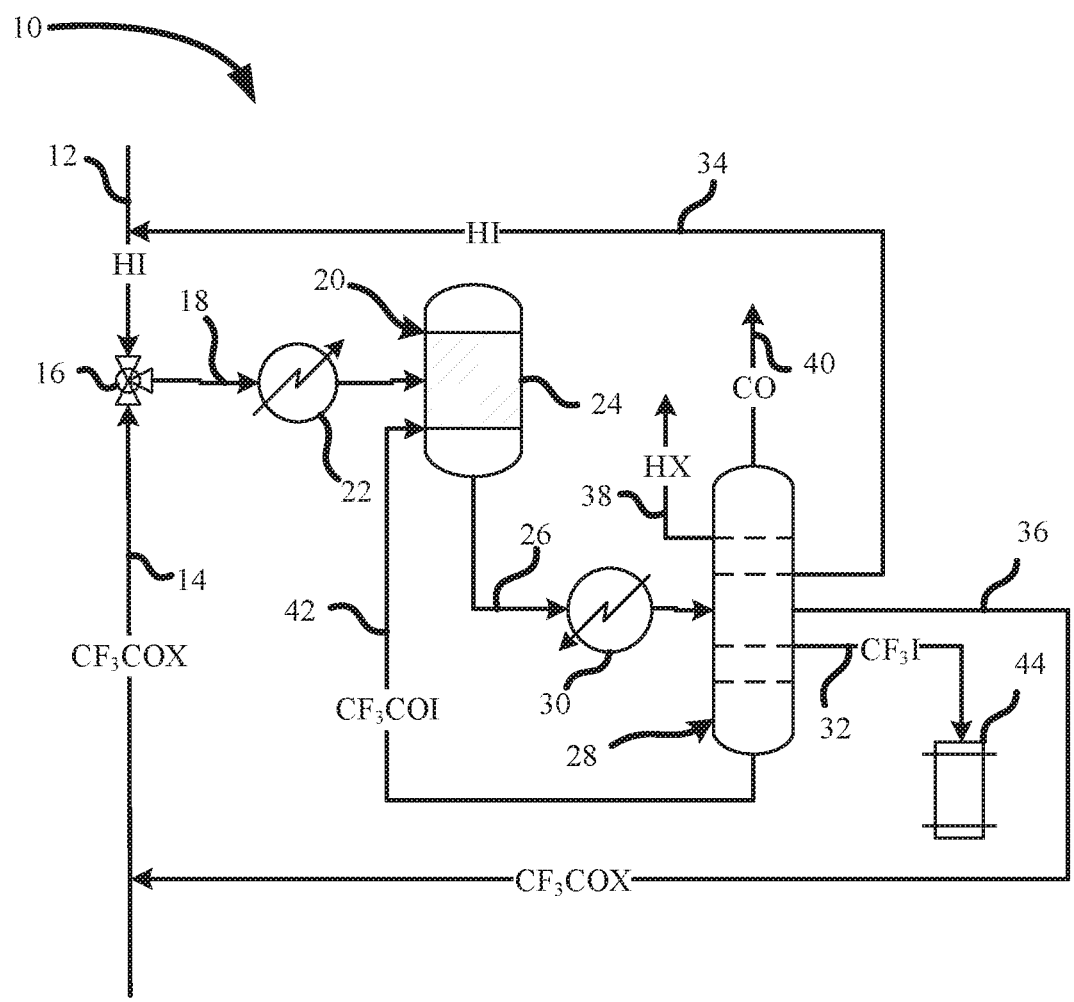

PROCESSES FOR PRODUCING TRIFLUOROIODOMETHANE

CROSS-REFERENCE TO RELATED APPLICATIONS

The present application claims the benefit under 35 U.S.C. § 119(e) of U.S. Provisional Patent Application No. 62/722,553, entitled PROCESSES FOR PRODUCING TRIFLUOROIODOMETHANE, filed Aug. 24, 2018, the entire disclosure of which is expressly incorporated herein.

FIELD

The present disclosure relates to processes for producing trifluoroiodomethane ($CF_3I$). Specifically, the present disclosure relates to gas-phase processes to produce trifluoroiodomethane.

BACKGROUND

Trifluoroiodomethane ($CF_3I$), also known as perfluoromethyliodide, trifluoromethyl iodide, or iodotrifluoromethane, is a useful compound in commercial applications, as a refrigerant or a fire suppression agent, for example. Trifluoroiodomethane is a low global warming potential molecule with almost no ozone depletion potential. Trifluoroiodomethane can replace more environmentally damaging materials.

Methods of preparing trifluoroiodomethane are known. For example, U.S. Pat. No. 7,196,236 (Mukhopadhyay et al.) discloses a catalytic process for producing trifluoroiodomethane using reactants comprising a source of iodine, at least a stoichiometric amount of oxygen, and a reactant $CF_3R$, where R is selected from the group consisting of —COOH, —COX, —CHO, —COOR$_2$, AND —SO$_2$X, where R$_2$ is alkyl group and X is a chlorine, bromine, or iodine. Hydrogen iodide, which may be produced by the reaction, can be oxidized by the at least a stoichiometric amount of oxygen, producing water and iodine for economic recycling.

In another example, U.S. Pat. No. 7,132,578 (Mukhopadhyay et al.) also discloses a catalytic, one-step process for producing trifluoroiodomethane from trifluoroacetyl chloride. However, the source of iodine, is iodine fluoride (IF). In contrast to hydrogen iodide, iodine fluoride is relatively unstable, decomposing above 0° C. to $I_2$ and $IF_5$. Iodine fluoride may also not be available in commercially useful quantities.

Some known methods of preparing trifluoroacetyl iodide include liquid-phase processes. Liquid-phase processes can require solvents that must be separated out and disposed of. The extra steps required for separation and disposal may make the processes less efficient.

Thus, there is a need to develop a more efficient process that may be scaled to produce commercial quantities of trifluoroiodomethane from relatively inexpensive raw materials.

SUMMARY

The present disclosure provides gas-phase processes for producing trifluoroiodomethane ($CF_3I$).

In one form thereof, the present disclosure provides a gas-phase process for producing trifluoroiodomethane, the process comprising providing a reactant stream comprising hydrogen iodide and trifluoroacetyl halide selected from the group consisting of trifluoroacetyl chloride, trifluoroacetyl fluoride, trifluoroacetyl bromide, and combinations thereof, and reacting the reactant stream in the presence of a catalyst at a temperature from about 200° C. to about 600° C. to produce a product stream comprising the trifluoroiodomethane.

In the providing step, the reactant stream may comprise less than about 500 ppm by volume of oxygen. In the providing step, the hydrogen iodide may comprise less than about 500 ppm by weight of water. In the providing step, a mole ratio of the hydrogen iodide to the trifluoroacetyl halide may be from about 0.1:1 to about 2.0:1. In the providing step, the mole ratio of the hydrogen iodide to the trifluoroacetyl halide may be from about 0.8:1 to about 1.5:1. In the providing step, the trifluoroacetyl halide may consist of trifluoroacetyl chloride.

In the reacting step, a contact time of the reactant stream with the catalyst may be from about 0.5 second to about 60 seconds. In the reacting step, the contact time of the reactant stream with the catalyst may be from about 10 seconds to about 50 seconds. In the reacting step, the catalyst may comprise at least one catalyst selected from the group of an activated carbon catalyst and a meso carbon catalyst. In the reacting step, the catalyst may consist essentially of at least one catalyst selected from the group of an activated carbon catalyst and a meso carbon catalyst. In the reacting step, the temperature may be from about 350° C. to about 400° C. The process may further comprise the additional step of heating the reactant stream to a temperature from about 80° C. to about 120° C. before reacting the reactant stream in the presence of the catalyst.

Organic compounds in the product stream may consist of, in GC area % of total organic compounds, from about 10% to about 99% trifluoroiodomethane, from about 1% to about 60% unreacted trifluoroacetyl halide, less than about 80% trifluoroacetyl iodide, and less than about 10% organic compounds other than trifluoroiodomethane, trifluoroacetyl halide, and trifluoroacetyl iodide. Organic compounds in the product stream may consist of, in GC area % of total organic compounds, from about 40% to about 99% trifluoroiodomethane, from about 1% to about 40% unreacted trifluoroacetyl halide, less than about 20% trifluoroacetyl iodide, and less than about 9% organic compounds other than trifluoroiodomethane, trifluoroacetyl halide, and trifluoroacetyl iodide. Organic compounds in the product stream may consist of, in GC area % of total organic compounds, from about 70% to about 99% trifluoroiodomethane, from about 1% to about 30% unreacted trifluoroacetyl halide, less than about 5% trifluoroacetyl iodide, and less than about 5% organic compounds other than trifluoroiodomethane, trifluoroacetyl halide, and trifluoroacetyl iodide.

The process may further comprise the additional steps of separating the unreacted trifluoroacetyl halide from the product stream, and returning the separated unreacted trifluoroacetyl halide to the reactant stream. The process may further comprise the additional step of separating the trifluoroacetyl iodide from the product stream. The process may further comprise the additional step of separating unreacted hydrogen iodide from the product stream and returning the unreacted hydrogen iodide to the reactant stream. The process may further comprise the additional step of separating hydrohalic acid and carbon monoxide from the product stream. The process may be a continuous process.

In another form thereof, the present disclosure provides a composition comprising a concentration of trifluoroiodomethane greater than about 99 wt. %.

The above mentioned and other features of the disclosure, and the manner of attaining them, will become more apparent and will be better understood by reference to the following description of embodiments taken in conjunction with the accompanying drawings.

BRIEF DESCRIPTION OF THE DRAWINGS

The FIGURE is a process flow diagram showing a process for manufacturing trifluoroiodomethane.

DETAILED DESCRIPTION

The present disclosure provides processes for the manufacture of trifluoroiodomethane that produce surprisingly good process yields starting from hydrogen iodide and trifluoroacetyl halide, such as trifluoroacetyl chloride. Such starting materials are relatively inexpensive and readily available in commercial quantities. The processes of this disclosure may be high-yielding, gas-phase processes that are amenable for the manufacture of trifluoroiodomethane on a commercial scale. The disclosed gas-phase processes require no solvents, further enhancing their commercial appeal.

As disclosed herein, the trifluoroiodomethane may be produced from a reactant stream comprising hydrogen iodide (HI) and trifluoroacetyl halide ($CF_3COX$). The hydrogen iodide and the trifluoroacetyl halide are anhydrous. It is preferred that there be as little water in the reactant stream as possible because any water in the reactant stream may hydrolyze some of the trifluoroacetyl halide and form the more thermodynamically favorable trifluoroacetic acid, rather than the desired trifluoroiodomethane.

The anhydrous hydrogen iodide is substantially free of water That is, any water in the anhydrous hydrogen iodide is in an amount by weight less than about 500 parts per million, about 300 ppm, about 200 ppm, about 100 ppm, about 50 ppm, about 30 ppm, about 20 ppm, about 10 ppm, about 5 ppm, about 3 ppm, about 2 ppm, or about 1 ppm, or less than any value defined between any two of the foregoing values. Preferably, the anhydrous hydrogen iodide comprises water by weight in an amount less than about 100 ppm. More preferably, the anhydrous hydrogen iodide comprises water by weight in an amount less than about 10 ppm. Most preferably, the anhydrous hydrogen iodide comprises water by weight in an amount less than about 1 ppm.

The reactant stream is substantially free of oxygen. That is, any oxygen in the reactant stream is in an amount by weight less than about 500 parts per million, about 300 ppm, about 200 ppm, about 100 ppm, about 50 ppm, about 30 ppm, about 20 ppm, about 10 ppm, about 5 ppm, about 3 ppm, about 2 ppm, or about 1 ppm, or less than any value defined between any two of the foregoing values. Preferably, the amount of oxygen by weight in the reactant stream is less than about 100 ppm. More preferably, the amount of oxygen by weight in the reactant stream is less than about 10 ppm. Most preferably, the amount of oxygen by weight in the reactant stream is less than about 1 ppm. It is preferred that there be as little oxygen in the reaction stream as possible because any oxygen in the reaction stream may oxidize at least some of the hydrogen iodide to form iodine and water before the hydrogen iodide can react to form trifluoroiodomethane. Even if running with an excess of hydrogen iodide, the water formed may hydrolyze the trifluoroacetyl halide and form the more thermodynamically favorable trifluoroacetic acid, rather than the desired trifluoroiodomethane, reducing the efficiency of the process.

The at least one trifluoroacetyl halide may be selected from the group consisting of trifluoroacetyl fluoride ($CF_3COF$), trifluoroacetyl chloride ($CF_3COCl$), trifluoroacetyl bromide ($CF_3COBr$), and any combinations thereof. Preferably, the at least one trifluoroacetyl halide comprises trifluoroacetyl chloride. More preferable, the at least one trifluoroacetyl halide consists essentially of trifluoroacetyl chloride. Most preferably, the at least one trifluoroacetyl halide consists of trifluoroacetyl chloride.

Trifluoroacetyl chloride, for example, is readily available in commercial quantities from Halocarbon Products Corporation, Peachtree Corners, Georgia, or from Solvay S.A., Brussels, Belgium, for example. Hydrogen iodide is commercially available or may be manufactured by, for example, reacting elemental iodine with hydrazine, distilling it from a solution of sodium iodide and phosphoric acid, or irradiating a mixture of hydrogen and elemental iodine with at a wavelength of about 578 nanometers.

In the reactant stream, a mole ratio of the hydrogen iodide to the trifluoroacetyl halide may be as low as about 0.1:1, about 0.2:1, about 0.3:1, about 0.4:1, about 0.5:1, about 0.6:1, about 0.7:1, about 0.8:1, about 0.9:1, about 0.95:1, about 0.99:1, or about 1:1, or as high as about 1.01:1, about 1.05:1, about 1.1:1, about 1.2:1, about 1.3:1, about 1.4:1, about 1.5:1, about 1.6:1, about 1.8:1, or about 2.0:1, or within any range defined between any two of the foregoing values, such as about 0.1:1 to about 2.0:1, about 0.5:1 to about 1.5:1, about 0.6:1 to about 1.4:1, about 0.7:1 to about 1.3:1, about 0.8:1 to about 1.2:1, about 0.9:1 to about 1.1:1, about 0.95:1 to about 1.05:1, about 0.99:1 to about 1.01:1, about 1:1 to about 2:1, about 0.8:1 to about 1.5:1, or about 0.95:1 to about 1.2:1, for example. Preferably, the mole ratio of the hydrogen iodide to the trifluoroacetyl halide may be from about 0.8:1 to about 1.5:1. More preferably, the mole ratio of the hydrogen iodide to the trifluoroacetyl halide may be from about 1:1 to about 1.2:1. Most preferably, the mole ratio of the hydrogen iodide to the trifluoroacetyl halide may be from about 0.9:1 to about 1.1:1.

The trifluoroacetyl halide and the hydrogen iodide forming the reactant stream may be individually pre-heated or pre-heated together before entering the reactor. The reactant stream may be pre-heated to a temperature as low as about 80° C., about 85° C., about 90° C., about 95° C., or about 100° C., or to a temperature as high as about 105° C., about 110° C., about 115° C., or about 120° C., or to a temperature within any range defined between any two of the foregoing values, such as about 80° C. to about 120° C., about 85° C. to about 115° C., about 90° C. to about 110° C., about 95° C. to about 105° C., or about 90° C. to about 100° C., for example. Preferably, the reactant stream may be pre-heated to a temperature from about 85° C. to about 115° C. More preferably, the reactant stream may be pre-heated to a temperature from about 90° C. to about 110° C. Most preferably, the reactant stream may be pre-heated to a temperature of about 100° C.

The hydrogen iodide and the trifluoroacetyl halide in the reactant stream react in the presence of a catalyst contained within a reactor to produce a product stream comprising trifluoroiodomethane and reaction by-products carbon monoxide (CO) and at least one hydrohalic acid (HX) according to Equation 1 below:

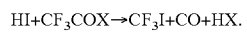
$$HI+CF_3COX \rightarrow CF_3I+CO+HX. \qquad \text{Eq. 1:}$$

The at least one hydrohalic acid may be selected from the group consisting of hydrofluoric acid (HF), hydrochloric acid (HCl), and hydrobromic acid (HBr).

The reactor may be a heated tube reactor comprising a tube containing the catalyst. The tube may be made of a metal such as stainless steel, nickel, and/or a nickel alloy, such as a nickel-molybdenum alloy, a nickel-chromium-molybdenum alloy, or a nickel-copper alloy. The tube within the reactor may be heated, thus also heating the catalyst. The reactor may be any type of packed bed reactor.

The reactant stream may be in contact with the catalyst for a contact time as short as about 0.5 seconds, about 1 second, about 2 seconds, about 3 seconds, about 5 seconds, about 8 seconds, about 10 seconds, about 12 seconds, or about 15 seconds, or as long as about 20 seconds, about 25 seconds, about 30 seconds, about 35 seconds, about 40 seconds, about 50 seconds or about 60 seconds, or for any contact time within any range defined between any two of the foregoing values, such as about 0.5 seconds to about 60 seconds, about 1 second to about 50 seconds, about 5 seconds to about 40 seconds, about 8 seconds to about 35 seconds, about 10 seconds to about 30 seconds, about 12 seconds to about 25 seconds, about 15 seconds to about 20 seconds, about 20 seconds to about 25 seconds, about 10 seconds to about 40 seconds, or about 10 seconds to about 30 seconds, for example. Preferably, the reactant stream may be in contact with the catalyst for a contact time from about 10 seconds to about 50 seconds. More preferably, the reactant stream may be in contact with the catalyst for a contact time from about 20 seconds to about 40 seconds. Most preferably, the reactant stream may be in contact with the catalyst for a contact time of from about 20 seconds to about 40 seconds.

The reactant stream may be heated to a temperature as low as about 200° C., about 250° C., about 300° C., about 325° C., about 330° C., about 340° C., about 350° C., or about 360° C., or to a temperature as high as about 370° C., about 380° C., about 390° C., about 400° C., about 450° C., about 475° C., about 500° C., about 525° C., about 550° C., about 575° C., or about 600° C. or to a temperature within any range defined between any two of the foregoing values, such as about 200° C. to about 600° C., about 325° C. to about 400° C., about 330° C. to about 390° C., about 340° C. to about 380° C., about 350° C. to about 370° C., or about 340° C. to about 360° C., for example. Preferably, the reactant stream may be heated to a temperature from about 325° C. to about 450° C. More preferably, the reactant stream may be heated to a temperature from about 350° C. to about 400° C. Most preferably, the reactant stream may be heated to a temperature from about 370° C. to about 390° C.

The catalyst is a carbon catalyst, such as and activated carbon, such as Norit-PK35, Calgon or Shirasagi, or a meso carbon catalyst, such as mesoC+™. The carbon catalyst may be in the form of carbon pellets, spheres, trilobes, or rings, for example. The activated carbon may have a surface area as small as about 100 square meters per gram (m²/g), about 200 m²/g, about 300 m²/g, about 400 m²/g, about 600 m²/g or about 800 m²/g, or as large as about 1,000 m²/g, about 1,200 m²/g, about 1,400 m²/g, about 1,600 m²/g, about 1,800 m²/g, or about 2,000 m²/g, or have a surface area within any range defined between any two of the foregoing values, such as about 100 m²/g to about 2,000 m²/g, about 400 m²/g to about 1,800 m²/g, about 600 m²/g to about 1,600 m²/g, about 800 m²/g to about 1,400 m²/g, about 1,000 m²/g to about 1,200 m²/g, or about 100 m²/g to about 400 m²/g, for example. Preferably, carbon catalyst has a surface area from about 800 m²/g to about 1,200 m²/g.

The carbon catalyst may have an average pore diameter as small as about 0.2 nanometers (nm), about 0.5 nm. about 1 nm, about 1.5 nm, about 2 nm, or about 2.5 nm, or as large as about 3 nm, about 5 nm, about 10 nm, about 15 nm, about 20 nm, or about 25 nm, or an average pore diameter within any range defined between any two of the foregoing values, such as about 0.2 nm to about 25 nm, about 0.2 nm to about 20 nm, about 1.0 nm to about 15 nm, about 1.5 nm to about 10 nm, about 2 nm to about 5 nm, or about 2.5 nm to about 3 nm, for example.

Pressure is not critical. Convenient operating pressures may range from about 100 KPa to about 200 KPa, and preferably around ambient pressure, or about 100 KPa.

In addition to trifluoroiodomethane, carbon monoxide, and hydrohalic acid, the product stream may further comprise unreacted trifluoroacetyl halide and hydrogen iodide. The product stream may even further comprise small amounts of other organic compounds, such as trifluoroacetyl iodide ($CF_3COI$).

The composition of the organic compounds in the product stream may be measured as by gas chromatography (GC) and gas chromatography-mass spectroscopy (GC-MS) analyses. Graph areas provided by the GC analysis for each of the organic compounds may be combined to provide a GC area percentage (GC area %) of the total organic compounds for each of the organic compounds as a measurement of the relative concentrations of the organic compounds in the product stream.

The concentration of trifluoroiodomethane in the product stream, in GC area % of total organic compounds, may be as low as about 10%, about 15%, about 20%, about 25%, about 30%, about 35%, about 40%, about 45%, about 50%, about 55% or about 60%, or may be as high as about 65%, about 70%, about 75%, about 80%, about 85%, about 90%, about 95%, about or 99% or within any range defined between any two of the foregoing values, such as about 10% to about 99%, about 20% to about 95%, about 30% to about 90%, about 40% to about 85%, about 45% to about 80%, about 50% to about 75%, about 55% to about 70%, about 60% to about 65%, about 90% to about 99% or about 95% to about 99%, for example. Preferably, the concentration of trifluoroiodomethane in the product stream may be from about 40% to about 99%. More preferably, the concentration of trifluoroiodomethane in the product stream may be from about 60% to about 99%. Most preferably, the concentration of trifluoroiodomethane in the product stream may be from about 70% to about 99%.

The concentration of unreacted trifluoroacetyl halide in the product stream, in GC area % of total organic compounds, may be as low as about 1%, about 5%, about 10%, about 15%, about 20%, about 25%, about 30%, or about 35%, or may be as high as about 40%, about 45%, about 50%, about 55%, about 60%, about 65%, about 70%, or about 75% or within any range defined between any two of the foregoing values, such as about 1% to about 75%, about 5% to about 70%, about 10% to about 65%, about 15% to about 60%, about 20% to about 55%, about 25% to about 50%, about 30% to about 45%, about 35% to about 40%, about 1% to about 5%, about 5% to about 40% or about 5% to about 60%, for example. Preferably, the concentration of unreacted trifluoroacetyl halide in the product stream may be from about 1% to about 60%. More preferably, the concentration of unreacted trifluoroacetyl halide in the product stream may be from about 1% to about 40%. Most preferably, the concentration of unreacted trifluoroacetyl halide in the product stream may be from about 1% to about 30%.

The concentration of trifluoroacetyl iodide in the product stream, in GC area % of total organic compounds, may be less than about 80%, about 70%, about 60%, about 50%, about 40%, about 30%, about 20%, about 18%, about 16%, about 14%, about 12%, about 10%, about 8%, about 6%, about 4%, about 3%, about 2%, or about 1%. Preferably, the concentration of trifluoroacetyl iodide in the product stream may be less than about 20%. More preferably, the concentration of trifluoroacetyl iodide in the product stream may be less than about 10%. Most preferably, the concentration of trifluoroacetyl iodide in the product stream may be less than about 5%.

The concentration of all other organic compounds in the product stream, in GC area % of total organic compounds, may be less than about 10%, about 9%, about 8%, about 7%, about 6%, about 5%, about 4%, about 3%, about 2%, about 1%, about 0.5%, or about 0.1%. Preferably, the concentration of all other organic compounds in the product stream may be less than about 9%. More preferably, the concentration of all other organic compounds in the product stream may be less than about 7%. Most preferably, the concentration of all other organic compounds in the product stream may be less than about 5%.

Alternatively stated, organic compounds in the product stream may consist of, in GC area % of total organic compounds, from about 10% to about 99% trifluoroiodomethane, from about 1% to about 60% unreacted trifluoroacetyl halide, less than about 80% trifluoroacetyl iodide, and less than about 10% organic compounds other than trifluoroiodomethane, trifluoroacetyl halide, and trifluoroacetyl iodide. It is also provided that organic compounds in the product stream may consist of from about 40% to about 99% trifluoroiodomethane, from about 1% to about 60% unreacted trifluoroacetyl halide, less than about 20% trifluoroacetyl iodide, and less than about 9% organic compounds other than trifluoroiodomethane, trifluoroacetyl halide, and trifluoroacetyl iodide. It is also provided that organic compounds in the product stream may consist of from about 60% to about 99% trifluoroiodomethane, from about 1% to about 40% unreacted trifluoroacetyl halide, less than about 10% trifluoroacetyl iodide, and less than about 7% organic compounds other than trifluoroiodomethane, trifluoroacetyl halide, and trifluoroacetyl iodide. It is also provided that organic compounds in the product stream may consist of from about 70% to about 99% trifluoroiodomethane, from about 1% to about 30% unreacted trifluoroacetyl halide, less than about 5% trifluoroacetyl iodide, and less than about 5% organic compounds other than trifluoroiodomethane, trifluoroacetyl halide, and trifluoroacetyl iodide.

The product stream may proceed directly to a distillation column. Alternatively, the product stream may pass through a heat exchanger to cool the product stream before the product stream is provided to the distillation column.

The distillation column may be configured for the separation of many of the by-products, reactants, and organic compounds described above from the trifluoroiodomethane to produce a purified product stream. The distillation column may be configured to separate and return the unreacted hydrogen iodide to the reactant stream and to separate and return the unreacted trifluoroacetyl halide to the reactant stream.

The distillation column may also be configured to separate the hydrohalic acid into a hydrohalic acid stream and the carbon monoxide into a carbon monoxide stream for sale, reuse elsewhere, or disposal. The distillation column may be further configured to separate and return the trifluoroacetyl iodide to the reactor. Alternatively, the trifluoroacetyl iodide flow may be directed to a storage tank. The purified product stream comprising the trifluoroiodomethane may be directed to a storage tank.

The concentration of the trifluoroiodomethane in the purified product stream may be greater than about 99%. Preferably, the concentration of the trifluoroiodomethane in the purified product stream may be greater than about 99.5%. More preferably, the concentration of the trifluoroiodomethane in the purified product stream may be greater than about 99.9%. Most preferably, the concentration of trifluoroiodomethane in the purified product stream may be greater than about 99.99%.

It has been found that reacting hydrogen iodide and trifluoroacetyl halide in the presence of the catalysts and at the temperatures described above may produce high conversion rates of the hydrogen iodide and trifluoroacetyl halide with a high selectivity in favor of trifluoroiodomethane. The gas-phase process described above produces surprisingly good process yields and is amenable for the manufacture of trifluoroiodomethane on a commercial scale.

The FIGURE is a process flow diagram showing a one-step, gas-phase process 10 for manufacturing trifluoroiodomethane. As shown in the FIGURE, the process 10 may comprise material flows of hydrogen iodide (HI) 12 and at least one trifluoroacetyl halide ($CF_3COX$) 14.

The flow of hydrogen iodide 12 and the flow of trifluoroacetyl halide 14 may be controlled by flowmeters or mass flow controllers (not shown) before combining in a mixer valve 16 to form a reactant stream 18. The reactant stream 18 may be provided directly to a reactor 20. Alternatively, the reactant stream 18 may pass through a preheater 22 to heat the reactant stream 18 before the reactant stream 18 is provided to the reactor 20.

The reactant stream 18 may react in the presence of a catalyst 24 contained within the reactor 20 to produce a product stream 26 comprising trifluoroiodomethane and reaction by-products carbon monoxide (CO) and at least one hydrohalic acid (HX) according to Equation 1 above.

The product stream 26 may proceed directly to a distillation column 28. Alternatively, the product stream 26 may pass through a heat exchanger 30 before the product stream 26 is provided to the distillation column 28, as shown in the FIGURE. The heat exchanger 30 may be configured to cool the product stream 26 before it enters the distillation column 28.

The distillation column 28 may be configured for the separation of many of the by-products, reactants, and organic compounds described above from the trifluoroiodomethane to produce a purified product stream 32. As shown in the FIGURE, the distillation column 28 may be configured to separate and return the unreacted hydrogen iodide to the flow of hydrogen iodide 12 for use in the reactant stream 18 in a hydrogen iodide flow 34 and to separate and return the unreacted trifluoroacetyl halide to the flow of trifluoroacetyl halide 14 for use in the reactant stream 18 in a trifluoroacetyl halide flow 36.

The distillation column 28 may also be configured to separate the hydrohalic acid into a hydrohalic acid stream 38 and the carbon monoxide into a carbon monoxide stream 40 for sale, reuse elsewhere, or disposal. The distillation column 28 may be further configured to separate and return the trifluoroacetyl iodide to the reactor 20 in a trifluoroacetyl iodide flow 42, as shown in the FIGURE. Alternatively, the trifluoroacetyl iodide flow 42 may be directed to a storage tank (not shown). The purified product stream 32 comprising the trifluoroiodomethane may be directed to a storage tank 44.

While this invention has been described as relative to exemplary designs, the present invention may be further modified within the spirit and scope of this disclosure.

Further, this application is intended to cover such departures from the present disclosure as come within known or customary practice in the art to which this invention pertains.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

EXAMPLES

Manufacture of Trifluoroiodomethane According to Equation 1

In this Example, the manufacture of trifluoroiodomethane from hydrogen iodide and trifluoroacetyl chloride according to Equation 1 described above is demonstrated. Equimolar amounts of trifluoroacetyl chloride and anhydrous hydrogen iodide were passed through a preheater and heated to a temperature of about 100° C. in a series of nine experiments. The heated reactants were then passed through a stainless tube 3/8 inch (9.5 mm) in diameter and 6 inches (152 mm) in length. The tube was heated to temperatures ranging from 350° C. to 380° C., depending on the experiment, and purged with nitrogen for at least one hour before each experiment to drive off any water. For each experiment, the tube contained one of several catalysts. Contact times were varied from 12 seconds to 30 seconds. All exiting vapors for each experiment were collected in a sample bags for GC and GC-MS analyses. The results are shown in Tables 1, 2, and 3.

Table 1 lists the reaction conditions (temperature, contact time, and catalyst used) for each of the nine experiments. Table 2 lists the GC area % of the primary organic compounds of interest corresponding to each of the nine experiments. Table 3 lists a conversion percentage and selectivity percentages for trifluoroiodomethane, trifluoroacetyl iodide, and the combination of trifluoroiodomethane and trifluoroacetyl iodide corresponding to each of the nine experiments. Conversion and selectivity percentages are based on the GC area % data.

As shown in Tables 1, 2, and 3, the process described above in reference to Equation 1 is able to produce trifluoroiodomethane with conversion percentages and selectivity percentages exceeding 90%. Thus, Tables 1, 2, and 3 demonstrate processes in accordance with this disclosure for the manufacture of trifluoroiodomethane that produce surprisingly good conversion rates and selectivities.

TABLE 1

Reaction Conditions

| Experiment Number | Temp. (° C.) | Contact Time (seconds) | Catalyst |
|---|---|---|---|
| 1 | 350 | 20 | Activated Shirasagi carbon |
| 2 | 350 | 20 | Activated carbon PCP-LS4X10 |
| 3 | 350 | 20 | Activated carbon PCP-LS4X10 |
| 4 | 380 | 12 | Activated Carbon Norit- PK35 |
| 5 | 380 | 30 | Activated Carbon Norit- PK35 |
| 6 | 350 | 30 | Activated Carbon Norit- PK35 |
| 7 | 350 | 20 | Activated Carbon Norit- PK35 |
| 8 | 350 | 12 | Activated Carbon Norit- PK35 |
| 9 | 325 | 12 | Activated Carbon Norit- PK35 |

TABLE 2

Products - GC Area %

| Experiment Number | $CF_3H$ | $CF_3Cl$ | $CF_3C(O)Cl$ | $CF_3I$ | $CF_3C(O)I$ | Others (sum) |
|---|---|---|---|---|---|---|
| 1 | 2.3 | | 58.22 | 31.37 | 6.18 | 1.93 |
| 2 | | | 35.09 | 56.12 | 3.81 | 4.98 |
| 3 | | 1.75 | 55.51 | 26.09 | 12.3 | 4.35 |
| 4 | | 6.06 | 16.92 | 73.07 | 1.34 | 2.61 |
| 5 | | 5.62 | 8.51 | 82.52 | 0.33 | 3.02 |
| 6 | | 5.3 | 26.62 | 67.42 | 0.22 | 0.44 |
| 7 | | 2.13 | 26.35 | 65.19 | 3.24 | 3.09 |
| 8 | 1.3 | | 29.66 | 49.44 | 15.76 | 3.88 |
| 9 | 0.27 | | 27.48 | 14.28 | 55.8 | 2.17 |

TABLE 3

Conv. and Sel. %

| Experiment Number | Conv. % | Sel. % $CF_3I$ Only | Sel. % $CF_3C(O)I$ Only | Sel. % $CF_3I$ + $CF_3C(O)I$ |
|---|---|---|---|---|
| 1 | 41.8 | 75.1 | 14.8 | 89.9 |
| 2 | 64.9 | 86.5 | 5.9 | 92.3 |
| 3 | 44.5 | 58.6 | 27.6 | 86.3 |
| 4 | 83.1 | 88.0 | 1.6 | 89.6 |
| 5 | 91.49 | 90.20 | 0.36 | 90.56 |
| 6 | 73.38 | 91.88 | 0.30 | 92.18 |
| 7 | 73.65 | 88.51 | 4.40 | 92.91 |
| 8 | 70.34 | 70.29 | 22.41 | 92.69 |
| 9 | 19.70 | 19.69 | 76.94 | 96.64 |

Example 2: Separation of Trifluoroiodomethane

In this Example, the separation of trifluoroiodomethane is demonstrated. A mixture containing 85 wt. % trifluoroiodomethane, 10 wt. % trifluoroacetyl iodide, and 5 wt. % carbon monoxide can be charged into a distillation column. The distillation column can include a 10 gallon reboiler, a 2-inch inside diameter 10-foot Pro-Pak® column from the Cannon Instrument Company, State College, Pa., and about 30 theoretical plates. The distillation column can be equipped with temperature, absolute pressure, and differential pressure transmitters. The distillation can be run at a pressure of about 275 KPa and a condenser at a temperature of about −13° C. to collect the trifluoroiodomethane.

ASPECTS

Aspect 1 is a gas-phase process for producing trifluoroiodomethane ($CF_3I$), the process comprising providing a reactant stream comprising hydrogen iodide and trifluoroacetyl halide selected from the group consisting of trifluoroacetyl chloride, trifluoroacetyl fluoride, trifluoroacetyl bromide, and combinations thereof; and reacting the reactant stream in the presence of a catalyst at a temperature from 200° C. to 600° C. to produce a product stream comprising the trifluoroiodomethane.

Aspect 2 is the process of Aspect 1, wherein in the providing step, the reactant stream comprises less than about 500 ppm by volume of oxygen.

Aspect 3 is the process of Aspect 1, wherein in the providing step, the reactant stream comprises less than about 100 ppm by volume of oxygen.

Aspect 4 is the process of Aspect 1, wherein in the providing step, the reactant stream comprises less than about 10 ppm by volume of oxygen.

Aspect 5 is the process of Aspect 1, wherein in the providing step, the reactant stream comprises less than about 1 ppm by volume of oxygen.

Aspect 6 is the process of any of Aspects 1-5, wherein in the providing step, the hydrogen iodide comprises less than about 500 ppm by weight of water.

Aspect 7 is the process of any of Aspects 1-5, wherein in the providing step, the hydrogen iodide comprises less than about 100 ppm by weight of water.

Aspect 8 is the process of any of Aspects 1-5, wherein in the providing step, the hydrogen iodide comprises less than about 10 ppm by weight of water.

Aspect 9 is the process of any of Aspects 1-5, wherein in the providing step, the hydrogen iodide comprises less than about 1 ppm by weight of water.

Aspect 10 is the process of any of Aspects 1-9, wherein in the providing step, a mole ratio of the hydrogen iodide to the trifluoroacetyl halide is from about 0.1:1 to about 2:1.

Aspect 11 is the process of any of Aspects 1-9, wherein in the providing step, a mole ratio of the hydrogen iodide to the trifluoroacetyl halide is from about 0.8:1 to about 1.5:1.

Aspect 12 is the process of any of Aspects 1-9, wherein in the providing step, a mole ratio of the hydrogen iodide to the trifluoroacetyl halide is from about 1:1 to about 1.2:1.

Aspect 13 is the process of any of Aspects 1-9, wherein in the providing step, a mole ratio of the hydrogen iodide to the trifluoroacetyl halide is about 1:1.

Aspect 14 is the process of any of Aspects 1-13, wherein in the providing step, the trifluoroacetyl halide comprises trifluoroacetyl chloride.

Aspect 15 is the process of any of Aspects 1-14, wherein in the providing step, the trifluoroacetyl halide comprises trifluoroacetyl fluoride.

Aspect 16 is the process of any of Aspects 1-15, wherein in the providing step, the trifluoroacetyl halide comprises trifluoroacetyl bromide.

Aspect 17 is the process of any of Aspects 1-13, wherein in the providing step, the trifluoroacetyl halide consists essentially of trifluoroacetyl chloride.

Aspect 18 is the process of any of Aspects 1-13, wherein in the providing step, the trifluoroacetyl halide consists of trifluoroacetyl chloride.

Aspect 19 is the process of any of Aspects 1-13, wherein in the providing step, the trifluoroacetyl halide consists essentially of trifluoroacetyl fluoride.

Aspect 20 is the process of any of Aspects 1-13, wherein in the providing step, the trifluoroacetyl halide consists of trifluoroacetyl fluoride.

Aspect 21 is the process of any of Aspects 1-13, wherein in the providing step, the trifluoroacetyl halide consists essentially of trifluoroacetyl bromide.

Aspect 22 is the process of any of Aspects 1-13, wherein in the providing step, the trifluoroacetyl halide consists of trifluoroacetyl bromide.

Aspect 23 is the process of any of Aspects 1-22, wherein in the step of reacting the reactant stream, a contact time of the reactant stream with the catalyst is from about 0.5 seconds to about 60 seconds.

Aspect 24 is the process of any of Aspects 1-22, wherein in the step of reacting the reactant stream, a contact time of the reactant stream with the catalyst is from about 10 seconds to about 50 seconds.

Aspect 25 is the process of any of Aspects 1-22, wherein in the step of reacting the reactant stream, a contact time of the reactant stream with the catalyst is from about 20 seconds to about 40 seconds.

Aspect 26 is the process of any of Aspects 1-22, wherein in the step of reacting the reactant stream, a contact time of the reactant stream with the catalyst is from about 25 seconds to about 35 seconds.

Aspect 27 is the process of any of Aspects 1-26, wherein in the reacting step, the temperature is from about 320° C. to about 450° C.

Aspect 28 is the process of any of Aspects 1-26, wherein in the reacting step, the temperature is from about 325° C. to about 400° C.

Aspect 29 is the process of any of Aspects 1-26, wherein in the reacting step, the temperature is from about 325° C. to about 375° C.

Aspect 30 is the process of any of Aspects 1-26, wherein in the reacting step, the temperature is about 350° C.

Aspect 31 is the process of any of Aspects 1-30, wherein in the reacting step, the catalyst comprises at least one catalyst selected from the group of an activated carbon catalyst and a meso carbon catalyst.

Aspect 32 is the process of any of Aspects 1-30, wherein in the reacting step, the catalyst consists essentially of at least one catalyst selected from the group of an activated carbon catalyst and a meso carbon catalyst.

Aspect 33 is the process of any of Aspects 1-30, wherein in the reacting step, the catalyst consists of at least one catalyst selected from the group of an activated carbon catalyst and a meso carbon catalyst.

Aspect 33 is the process of any of Aspects 1-30, wherein in the reacting step, the catalyst comprises an activated carbon catalyst.

Aspect 34 is the process of any of Aspects 1-30, wherein in the reacting step, the catalyst consists essentially of an activated carbon catalyst.

Aspect 35 is the process of any of Aspects 1-30, wherein in the reacting step, the catalyst consists of an activated carbon catalyst.

Aspect 36 is the process of any of Aspects 1-30, wherein in the reacting step, the catalyst comprises a meso carbon catalyst.

Aspect 37 is the process of any of Aspects 1-30, wherein in the reacting step, the catalyst consists essentially of a meso carbon catalyst.

Aspect 38 is the process of any of Aspects 1-30, wherein in the reacting step, the catalyst consists of a meso carbon catalyst.

Aspect 39 is the process of any of Aspects 1-38, wherein the process is a continuous process.

Aspect 40 is the process of any of Aspects 1-39, further comprising the additional step of heating the reactant stream to a temperature from about 80° C. to about 120° C. before reacting the reactant stream in the presence of the catalyst.

Aspect 41 is the process of any of Aspects 1-40, wherein organic compounds in the product stream consist of, in GC area % of total organic compounds, from about 10% to about 99% trifluoroiodomethane, from about 1% to about 60% unreacted trifluoroacetyl halide, less than about 80% trifluoroacetyl iodide, and less than about 10% organic compounds other than trifluoroiodomethane, trifluoroacetyl halide, and trifluoroacetyl iodide.

Aspect 42 is the process of any of Aspects 1-40, wherein organic compounds in the product stream consist of, in GC area % of total organic compounds, from about 40% to about 99% trifluoroiodomethane, from about 1% to about 40% unreacted trifluoroacetyl halide, less than about 20% trifluoroacetyl iodide, and less than about 9% organic compounds other than trifluoroiodomethane, trifluoroacetyl halide, and trifluoroacetyl iodide.

Aspect 43 is the process of any of Aspects 1-40, wherein organic compounds in the product stream consist of, in GC area % of total organic compounds, from about 70% to about 99% trifluoroiodomethane, from about 1% to about 30% unreacted trifluoroacetyl halide, less than about 5% trifluoroacetyl iodide, and less than about 5% organic compounds other than trifluoroiodomethane, trifluoroacetyl halide, and trifluoroacetyl iodide.

Aspect 44 is the process of any of Aspects 41-43, further comprising the additional step of separating the trifluoroacetyl iodide from the product stream.

Aspect 45 is the process of any of Aspects 1-44, further comprising the additional steps of separating the unreacted trifluoroacetyl halide from the product stream, and returning the separated unreacted trifluoroacetyl halide to the reactant stream.

Aspect 46 is the process of any of Aspects 1-45, further comprising the additional steps of separating unreacted hydrogen iodide from the product stream and returning the unreacted hydrogen iodide to the reactant stream.

Aspect 47 is the process of any of Aspects 1-46, further comprising the additional step of separating hydrohalic acid and carbon monoxide from the product stream.

Aspect 48 is the process of any of Aspects 1-47, wherein a concentration of the trifluoroiodomethane in the product stream may be greater than about 99 wt. %.

Aspect 49 is the process of any of Aspects 1-47, wherein a concentration of the trifluoroiodomethane in the final product stream may be greater than about 99.5 wt. %.

Aspect 50 is the process of any of Aspects 1-47, wherein a concentration of the trifluoroiodomethane in the final product stream may be greater than about 99.9 wt. %.

Aspect 52 is the process of any of Aspects 1-47, wherein a concentration of the trifluoroiodomethane in the final product stream may be greater than about 99.99 wt. %.

Aspect 52 is a composition produced by a process according to any of Aspects 1-48, the composition comprising a concentration of trifluoroiodomethane greater than about 99 wt. %.

Aspect 53 is a gas-phase process for producing trifluoroiodomethane ($CF_3I$), the process comprising providing a reactant stream comprising hydrogen iodide and trifluoroacetyl halide selected from the group consisting of trifluoroacetyl chloride, trifluoroacetyl fluoride, trifluoroacetyl bromide, and combinations thereof; and reacting the reactant stream in the presence of an activated carbon catalyst to produce a product stream comprising the trifluoroiodomethane, the activated carbon catalyst including a surface area from about 800 $m^2/g$ to about 2,000 $m^2/g$ and an average pore diameter of about 0.2 nm to about 25 nm.

Aspect 54 is a gas-phase process for producing trifluoroiodomethane ($CF_3I$), the process comprising providing a reactant stream comprising hydrogen iodide and trifluoroacetyl bromide; and reacting the reactant stream in the presence of an activated carbon catalyst to produce a product stream comprising the trifluoroiodomethane, the activated carbon catalyst including a surface area from about 800 $m^2/g$ to about 2,000 $m^2/g$ and an average pore diameter of about 0.2 nm to about 25 nm.

Aspect 55 is a gas-phase process for producing trifluoroiodomethane ($CF_3I$), the process comprising providing a reactant stream comprising hydrogen iodide and trifluoroacetyl halide selected from the group consisting of trifluoroacetyl chloride, trifluoroacetyl fluoride, trifluoroacetyl bromide, and combinations thereof; and reacting the reactant stream in the presence of an activated carbon catalyst to produce a product stream comprising the trifluoroiodomethane, the reactant stream comprising less than about 500 ppm by volume of oxygen.

Aspect 56 is a gas-phase process for producing trifluoroiodomethane ($CF_3I$), the process comprising providing a reactant stream comprising hydrogen iodide and trifluoroacetyl halide selected from the group consisting of trifluoroacetyl chloride, trifluoroacetyl fluoride, trifluoroacetyl bromide, and combinations thereof; and reacting the reactant stream in the presence of a catalyst at a temperature from about 200° C. to about 600° C., for a contact time from about 0.5 seconds to about 60 seconds to produce a product stream comprising the trifluoroiodomethane, wherein in the providing step, a mole ratio of the hydrogen iodide to the trifluoroacetyl halide is from about 0.1:1 to about 2:1.

Aspect 57 is a gas-phase process for producing trifluoroiodomethane ($CF_3I$), the process comprising providing a reactant stream comprising hydrogen iodide and trifluoroacetyl chloride; and reacting the reactant stream in the presence of a catalyst at a temperature from about 325° C. to about 450° C., for a contact time from about 10 seconds to about 50 seconds to produce a product stream comprising the trifluoroiodomethane, wherein in the providing step, a mole ratio of the hydrogen iodide to the trifluoroacetyl halide is from about 0.8:1 to about 1.5:1.

Aspect 58 is a gas-phase process for producing trifluoroiodomethane ($CF_3I$), the process comprising providing a reactant stream comprising hydrogen iodide and trifluoroacetyl chloride; and reacting the reactant stream in the presence of a catalyst at a temperature from about 325° C. to about 450° C., for a contact time from about 10 seconds to about 50 seconds to produce a product stream comprising the trifluoroiodomethane, wherein in the providing step, a mole ratio of the hydrogen iodide to the trifluoroacetyl halide is from about 0.8:1 to about 1.5:1.

Aspect 59 is a gas-phase process for producing trifluoroiodomethane ($CF_3I$), the process comprising providing a reactant stream comprising hydrogen iodide and trifluoroacetyl chloride; and reacting the reactant stream in the presence of a catalyst at a temperature from about 350° C. to about 400° C., for a contact time from about 20 seconds to about 40 seconds to produce a product stream comprising the trifluoroiodomethane, wherein in the providing step, a mole ratio of the hydrogen iodide to the trifluoroacetyl halide is from about 1:1 to about 1.2:1.

Aspect 60 is a gas-phase process for producing trifluoroiodomethane ($CF_3I$), the process comprising providing a reactant stream comprising hydrogen iodide and trifluoroacetyl chloride; and reacting the reactant stream in the presence of a catalyst at a temperature from about 370° C. to about 390° C., for a contact time from about 25 seconds to about 35 seconds to produce a product stream comprising the trifluoroiodomethane, wherein in the providing step, a mole ratio of the hydrogen iodide to the trifluoroacetyl halide is from about 0.9 to about 1.1:1.

Aspect 61 is the process of any of Aspects 56-60, wherein the catalyst consists essentially of an activated carbon catalyst.

Aspect 61 is the process of any of Aspects 56-60, wherein the catalyst consists essentially of a meso carbon catalyst.

What is claimed is:

1. A gas-phase process for producing trifluoroiodomethane ($CF_3I$), the process comprising:
providing a reactant stream comprising hydrogen iodide and trifluoroacetyl halide selected from the group consisting of trifluoroacetyl chloride, trifluoroacetyl fluoride, trifluoroacetyl bromide, and combinations thereof, the reactant stream comprising less than about 500 ppm by volume of oxygen; and
reacting the reactant stream in the presence of a catalyst at a reaction temperature from about 200° C. to about 600° C. to produce a product stream comprising the trifluoroiodomethane, unreacted hydrogen iodide and unreacted trifluoroacetyl halide.

2. The process of claim 1, wherein in the providing step, the hydrogen iodide comprises less than about 100 ppm by weight of water.

3. The process of claim 1, wherein in the providing step, a mole ratio of the hydrogen iodide to the trifluoroacetyl halide is from about 0.1:1 to about 2:1.

4. The process of claim 1, wherein in the providing step, the trifluoroacetyl halide comprises trifluoroacetyl chloride.

5. The process of claim 1, wherein in the reacting step, a contact time of the reactant stream with the catalyst is from about 0.5 second to about 60 seconds.

6. The process of claim 5, wherein in the reacting step, the contact time of the reactant stream with the catalyst is from about 20 seconds to about 40 seconds.

7. The process of claim 1, wherein in the reacting step, the catalyst comprises an activated carbon catalyst, a meso carbon catalyst, or any combination thereof.

8. The process of claim 7, wherein in the reacting step, the catalyst consists essentially of at least one catalyst selected from the group consisting of an activated carbon catalyst and a meso carbon catalyst.

9. The process of claim 1, wherein in the reacting step, the reaction temperature is from about 370° C. to about 390° C., and in the providing step, the trifluoroacetyl halide consists essentially of trifluoroacetyl chloride, and a mole ratio of the hydrogen iodide to the trifluoroacetyl chloride is from about 0.9:1 to about 1.1:1.

10. The process of claim 9, wherein in the providing step, the reactant stream comprising less than about 10 ppm by volume of oxygen.

11. The process of claim 1, wherein the product stream further comprises trifluoroacetyl iodide, and wherein the organic compounds in the product stream consist of, in GC area % of total organic compounds, from about 70% to about 99% trifluoroiodomethane, from about 1% to about 30% unreacted trifluoroacetyl halide, less than about 5% trifluoroacetyl iodide, and less than about 5% organic compounds other than trifluoroiodomethane, trifluoroacetyl halide, and trifluoroacetyl iodide.

12. The process of claim 1, further comprising additional steps of:
separating the unreacted trifluoroacetyl halide from the product stream; and
returning the separated unreacted trifluoroacetyl halide to the reactant stream.

13. The process of claim 1, wherein the product stream further comprises trifluoroacetyl iodide, the process further comprising an additional step of separating the trifluoroacetyl iodide from the product stream and returning the separated trifluoroacetyl iodide to the reactant stream.

14. The process of claim 1, further comprising an additional step of separating unreacted hydrogen iodide from the product stream and returning the unreacted hydrogen iodide to the reactant stream.

15. The process of claim 1, wherein the process is a continuous process.

16. The process of claim 1, wherein in the providing step, the reactant stream comprising less than about 100 ppm by volume of oxygen.

17. The process of claim 16, wherein in the providing step, the reactant stream comprising less than about 50 ppm by volume of oxygen.

18. The process of claim 17, wherein in the providing step, the reactant stream comprising less than about 10 ppm by volume of oxygen.

19. The process of claim 18, wherein in the providing step, the reactant stream comprising less than about 1 ppm by volume of oxygen.

20. A gas-phase process for producing trifluoroiodomethane ($CF_3I$), the process comprising:
providing a reactant stream comprising hydrogen iodide and trifluoroacetyl halide selected from the group consisting of trifluoroacetyl chloride, trifluoroacetyl fluoride, trifluoroacetyl bromide, and combinations thereof;
heating the reactant stream to a temperature from about 80° C. to about 120° C. before reacting the reactant stream in the presence of the catalyst; and
reacting the reactant stream in the presence of a catalyst at a reaction temperature from about 200° C. to about 600° C. to produce a product stream comprising the trifluoroiodomethane.

21. The process of claim 20, wherein in the providing step, the trifluoroacetyl halide consists essentially of trifluoroacetyl chloride, and a mole ratio of the hydrogen iodide to the trifluoroacetyl chloride is from about 0.9:1 to about 1.1:1; in the heating step, the reactant stream is heated to a temperature from about 90° C. to about 110° C. before reacting the reactant stream in the presence of the catalyst; and in the reacting step, the reaction temperature is from about 370° C. to about 390° C.

22. The process of claim 21, wherein in the reacting step, the catalyst consists essentially of at least one catalyst selected from the group consisting of an activated carbon catalyst and a meso carbon catalyst.

23. A gas-phase process for producing trifluoroiodomethane ($CF_3I$), the process comprising:
providing a reactant stream comprising hydrogen iodide and trifluoroacetyl halide selected from the group consisting of trifluoroacetyl chloride, trifluoroacetyl fluoride, trifluoroacetyl bromide, and combinations thereof;
reacting the reactant stream in the presence of a catalyst at a reaction temperature from about 200° C. to about 600° C. to produce a product stream comprising the trifluoroiodomethane, hydrohalic acid and carbon monoxide; and
separating hydrohalic acid and carbon monoxide from the product stream.

24. The process of claim 14, wherein in the providing step, the trifluoroacetyl halide consists essentially of trifluoroacetyl chloride, and a mole ratio of the hydrogen iodide to the trifluoroacetyl chloride is from about 0.9:1 to about 1.1:1; and in the reacting step, the reaction temperature is from about 370° C. to about 390° C.

25. The process of claim 24, wherein in the reacting step, the catalyst consists essentially of at least one catalyst selected from the group consisting of an activated carbon catalyst and a meso carbon catalyst.

* * * * *